US012773137B2

United States Patent
Kang et al.

(12) United States Patent
(10) Patent No.: US 12,773,137 B2
(45) Date of Patent: Oct. 27, 2026

(54) SENSOR UNIT FOR MEASURING BIOMETRIC INFORMATION

(71) Applicant: I-SENS, INC., Seoul (KR)

(72) Inventors: Young Jea Kang, Seoul (KR); Hyun Ho Choi, Seoul (KR); Su Jin Lee, Seoul (KR)

(73) Assignee: I-SENS, INC., Seoul (KR)

( * ) Notice: Subject to any disclaimer, the term of this patent is extended or adjusted under 35 U.S.C. 154(b) by 357 days.

(21) Appl. No.: 18/575,750

(22) PCT Filed: Nov. 11, 2021

(86) PCT No.: PCT/KR2021/016423

§ 371 (c)(1),
(2) Date: Dec. 29, 2023

(87) PCT Pub. No.: WO2023/277273

PCT Pub. Date: Jan. 5, 2023

(65) Prior Publication Data

US 2024/0245325 A1 Jul. 25, 2024

(30) Foreign Application Priority Data

Jun. 29, 2021 (KR) ........................ 10-2021-0084704

(51) Int. Cl.
*A61B 5/145* (2006.01)
*A61B 5/00* (2006.01)

(52) U.S. Cl.
CPC ...... *A61B 5/14532* (2013.01); *A61B 5/14503* (2013.01); *A61B 5/6832* (2013.01); *A61B 2560/045* (2013.01)

(58) Field of Classification Search
CPC ... A61B 5/145; A61B 5/1459; A61B 5/14532; A61B 5/14503; A61B 5/14507;
(Continued)

(56) References Cited

U.S. PATENT DOCUMENTS 12,396,665 B2 8/2025 Chae et al.
2008/0242961 A1* 10/2008 Brister ............... A61B 5/14532 600/345
(Continued)

FOREIGN PATENT DOCUMENTS

EP 3 831 298 6/2021
JP 2009-509166 3/2009
(Continued)

OTHER PUBLICATIONS

Office Action (1st) dated Oct. 14, 2025 for Japanese Patent Application No. 2023-580896 and its English translation provided by Applicant's foreign counsel.
(Continued)

*Primary Examiner* — Chu Chuan Liu
(74) *Attorney, Agent, or Firm* — WOMBLE BOND DICKINSON (US) LLP

(57) ABSTRACT

A sensor unit according to the present invention is attached to the skin of a user to measure biometric information of the user, the sensor unit characterized by comprising: a sensor including a sensor body, an insertion part which is connected to the sensor body and can be inserted into the skin of the user, and a sensing unit provided at one side of the insertion part to measure biometric information; and a sensor unit housing on which the sensor is mounted, and which has a needle that can be inserted into the skin of the user together with the insertion part and an insertion hole through which the insertion part can pass, the sensor unit housing being attached to the skin of the user, wherein the insertion part is inserted into an incision part formed in the skin of the user by the needle together with the needle, and changes in inclination with respect to the sensor body so that the needle is separated from the skin of the user and then is inclined with respect to the longitudinal central axis of the incision part.

9 Claims, 11 Drawing Sheets

(58) Field of Classification Search

CPC ............ A61B 5/14539; A61B 5/14535; A61B 5/14542; A61B 5/14546; A61B 5/6832; A61B 5/262; A61B 5/6848; A61B 5/6833; A61B 5/6849; A61B 2560/045; A61B 2560/0412; A61B 2560/0443; A61B 2560/0462; A61B 2560/0209

See application file for complete search history.

(56) References Cited

U.S. PATENT DOCUMENTS

| | | | | |
|---|---|---|---|---|
| 2016/0058344 | A1* | 3/2016 | Peterson | A61B 5/14532<br>600/347 |
| 2019/0239779 | A1 | 8/2019 | Chase | |

FOREIGN PATENT DOCUMENTS

| | | |
|---|---|---|
| JP | 2020-520284 | 7/2020 |
| KR | 10-2013-0103410 | 9/2013 |
| KR | 10-2017-0117183 | 10/2017 |
| KR | 10-2020-0014002 | 2/2020 |
| WO | 01/41643 | 6/2001 |

OTHER PUBLICATIONS

Extended European Search Report dated Mar. 18, 2025 for European Patent Application No. 21948573.7.

International Search Report for PCT/KR2021/016423 mailed on Oct. 12, 2022 and its English translation from WIPO (now published as WO 2023/277273).

Written Opinion of the International Searching Authority for PCT/KR2021/016423 mailed on Oct. 12, 2022 and its English translation from WIPO (now published as WO 2023/277273).

* cited by examiner

[Fig. 1]
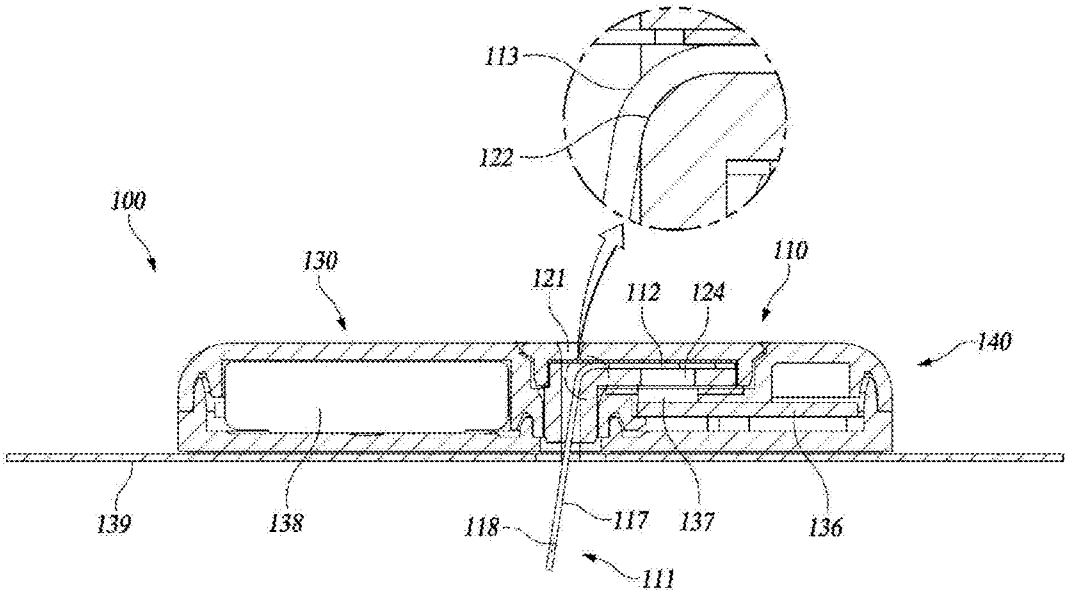
[Fig. 2]
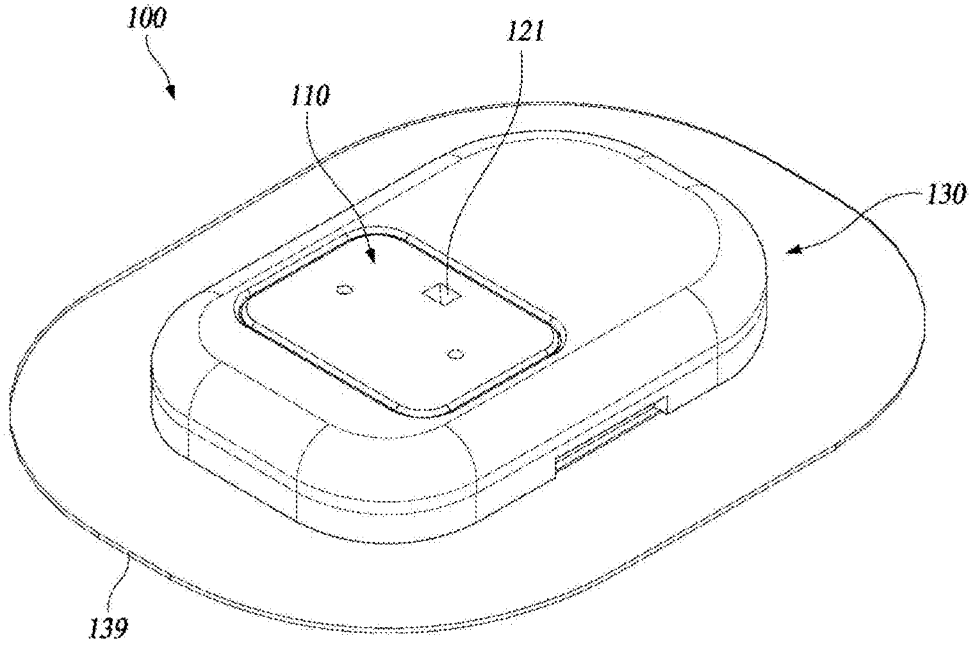

[Fig. 3]
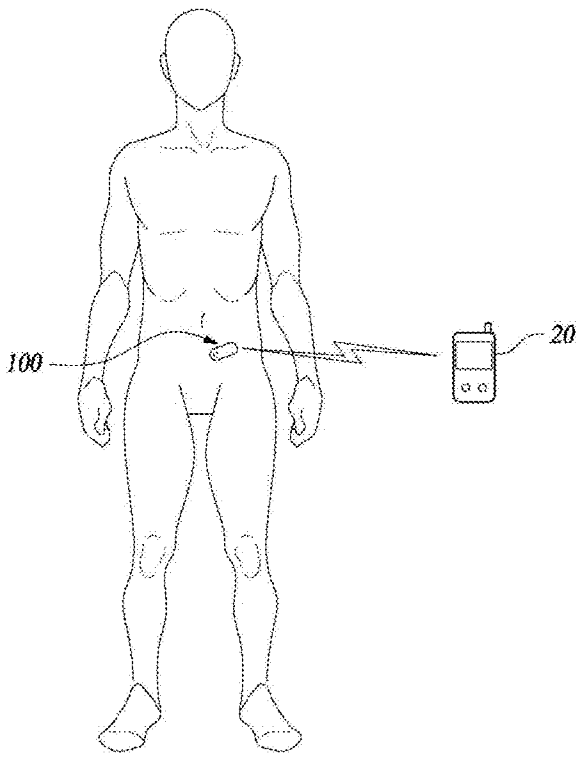
[Fig. 4]
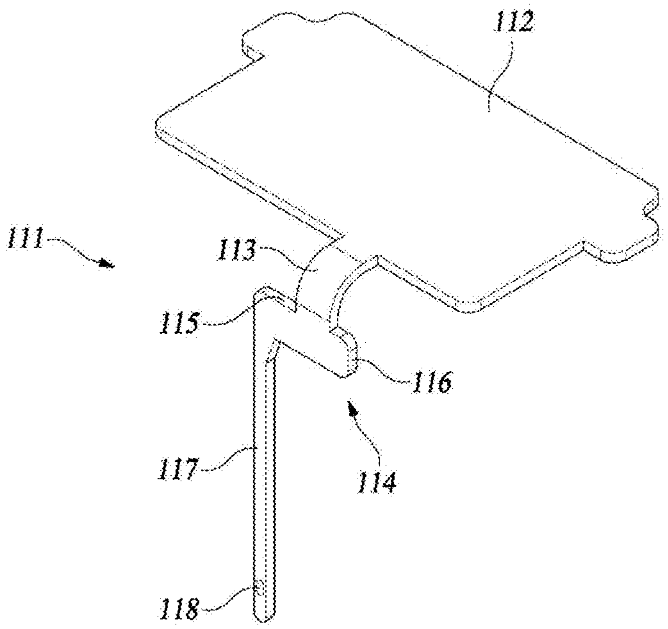

[Fig. 5]
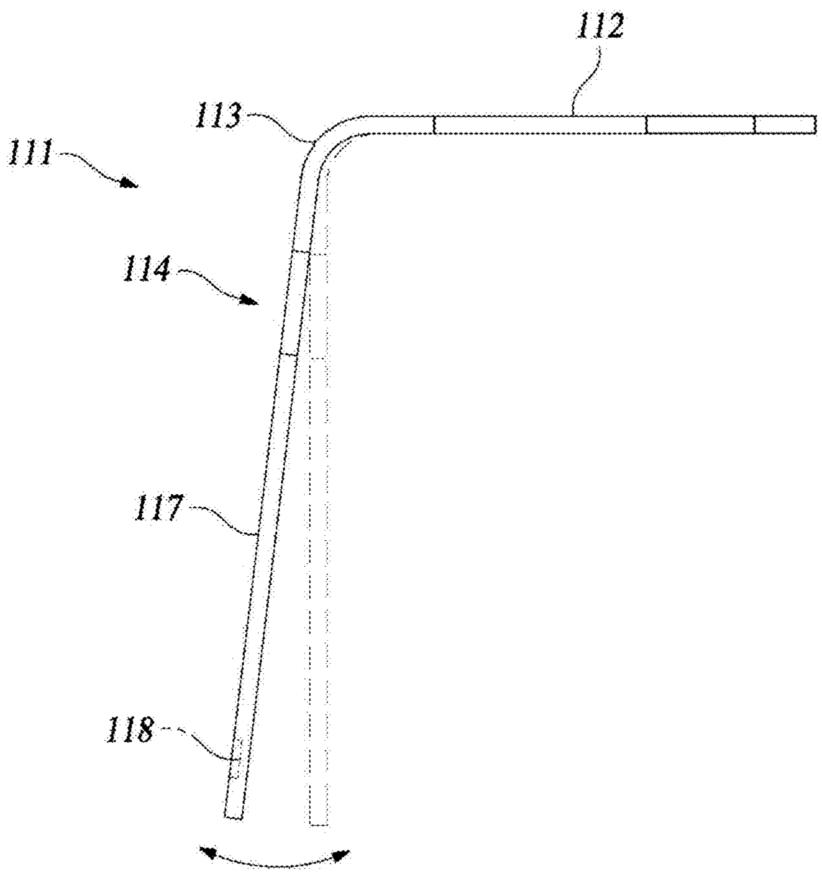

[Fig. 6]
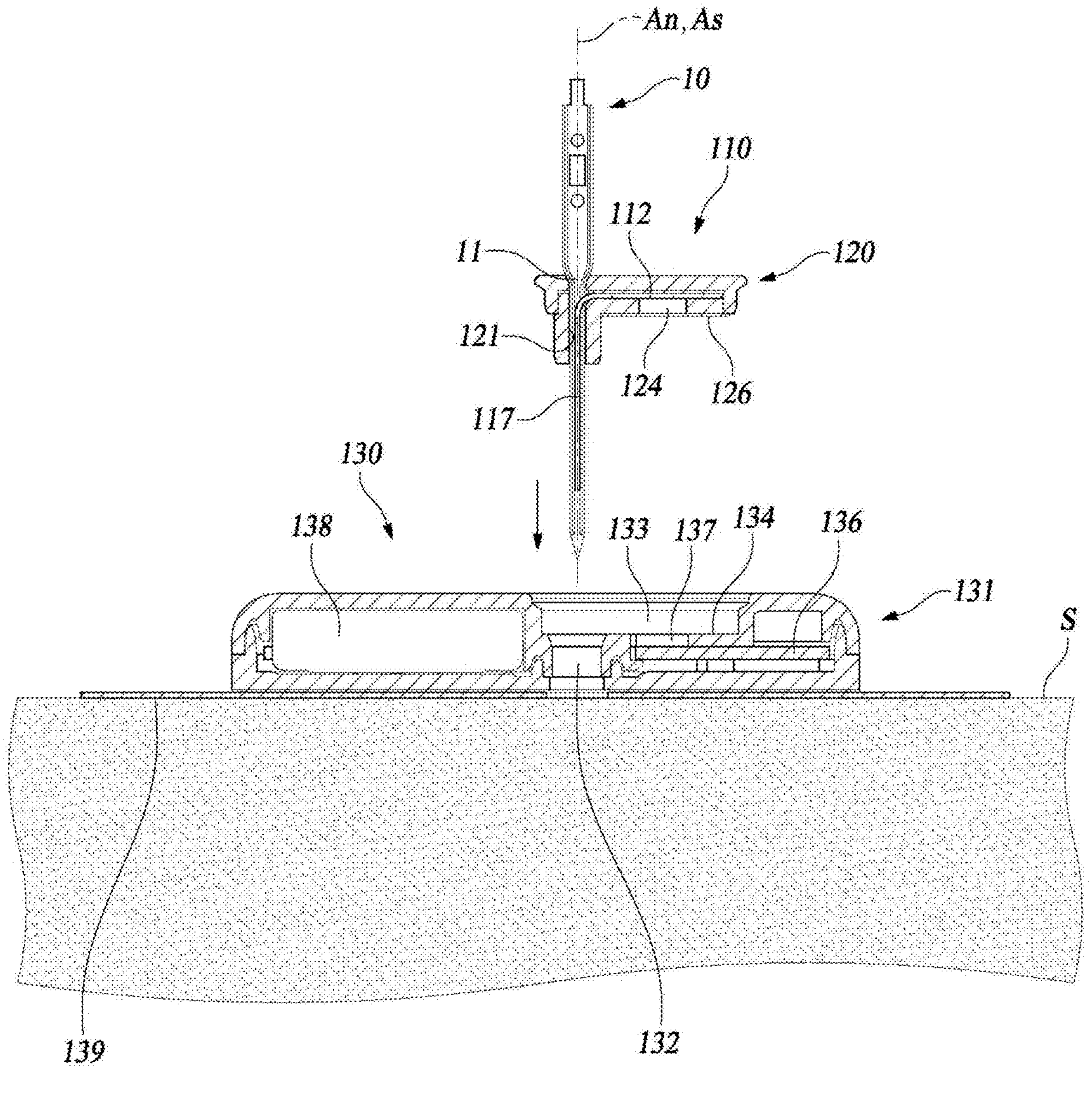

[Fig. 7]
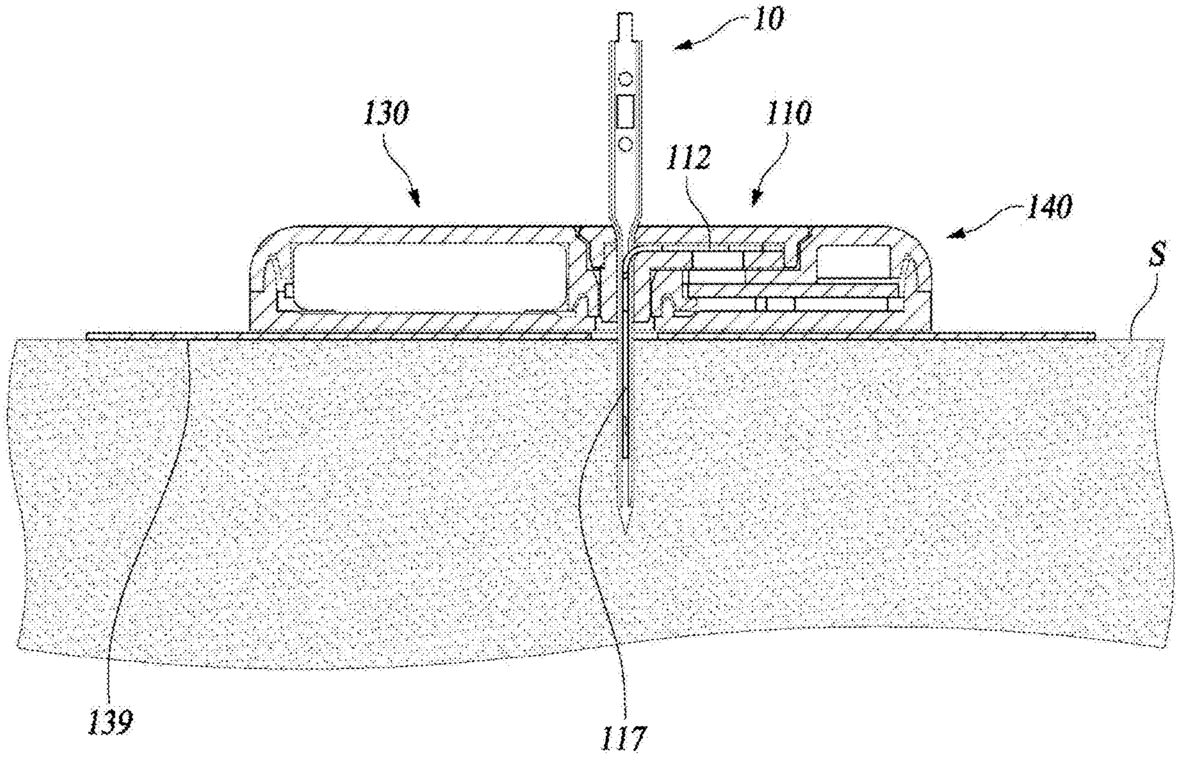

[Fig. 8]
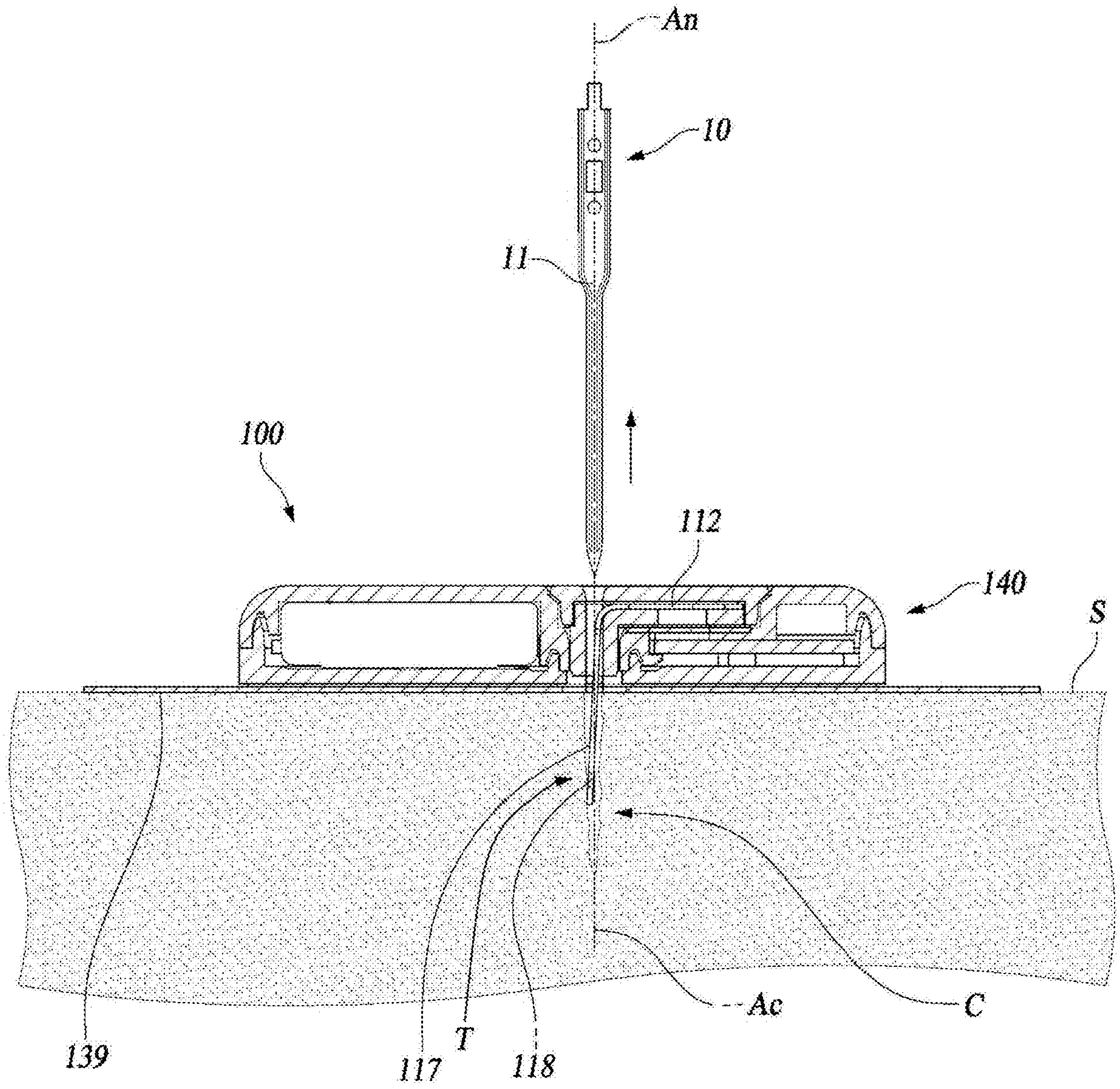

[Fig. 9]
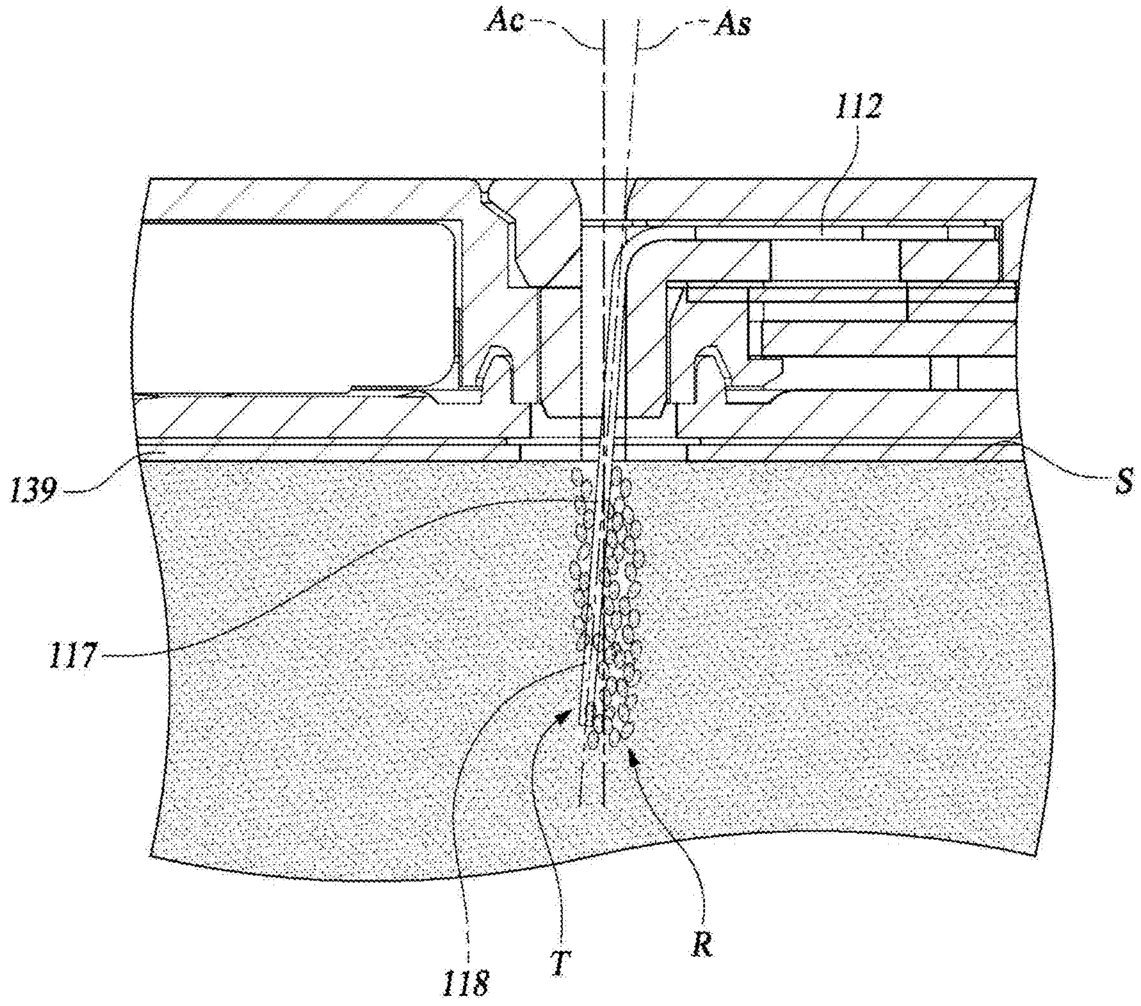

[Fig. 10]
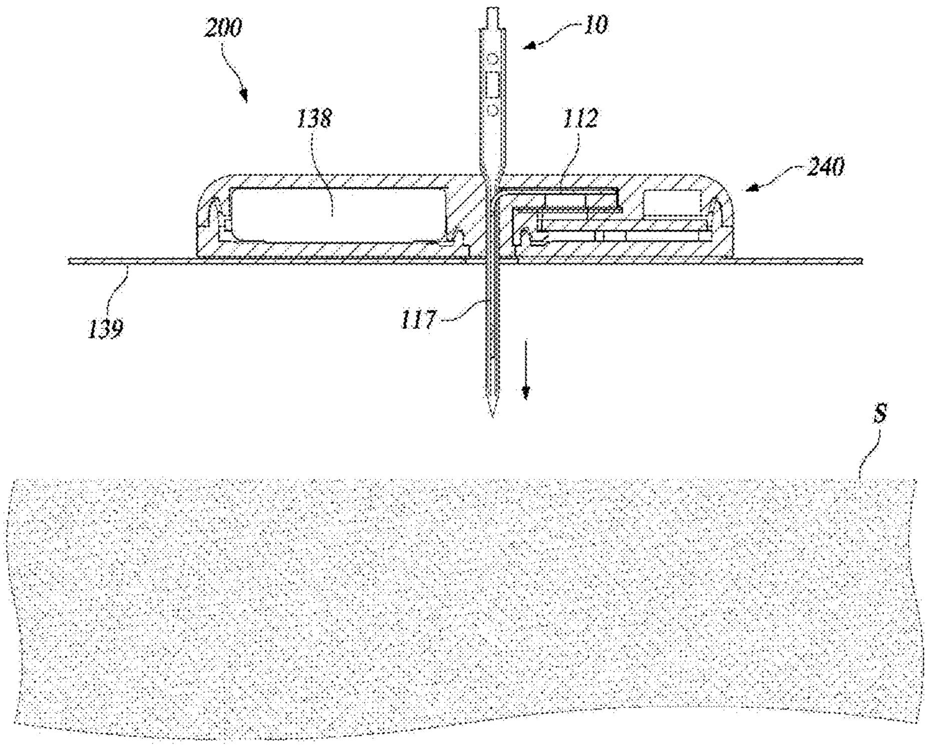
[Fig. 11]
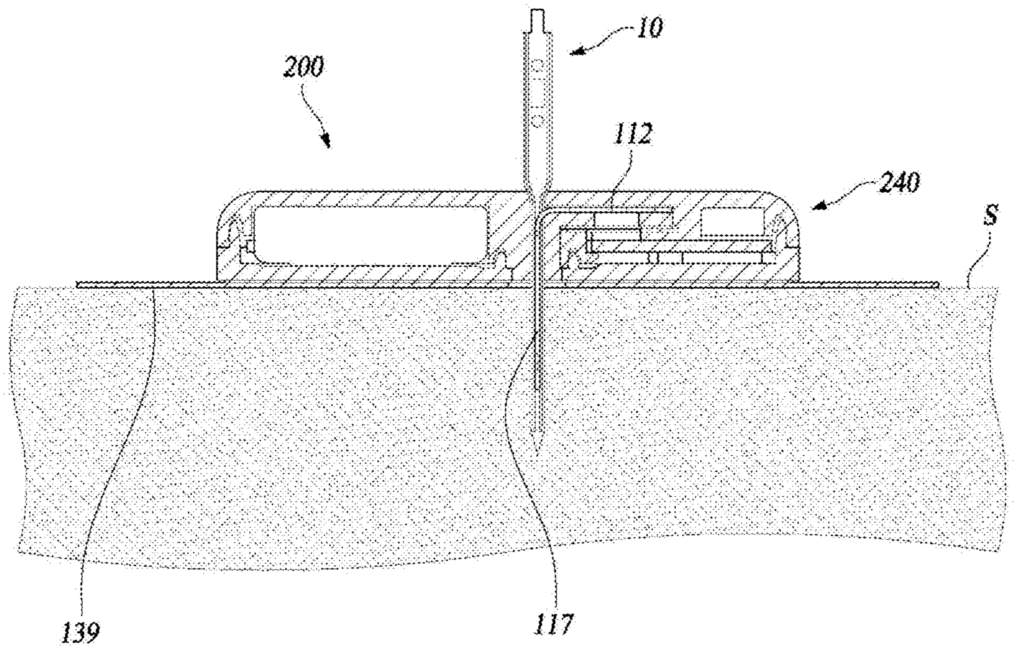

[Fig. 12]
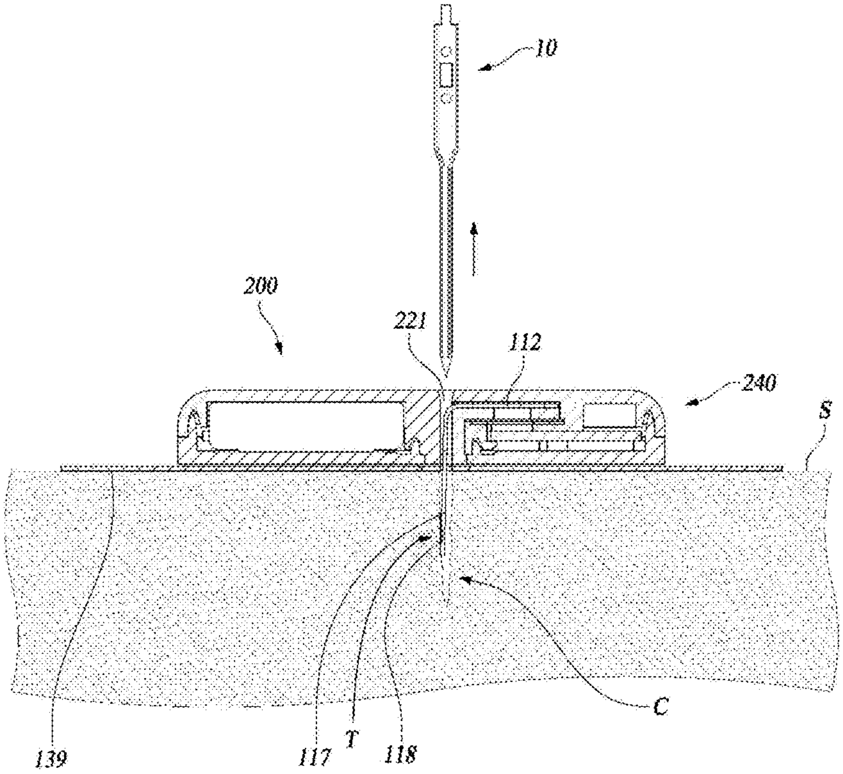
[Fig. 13]
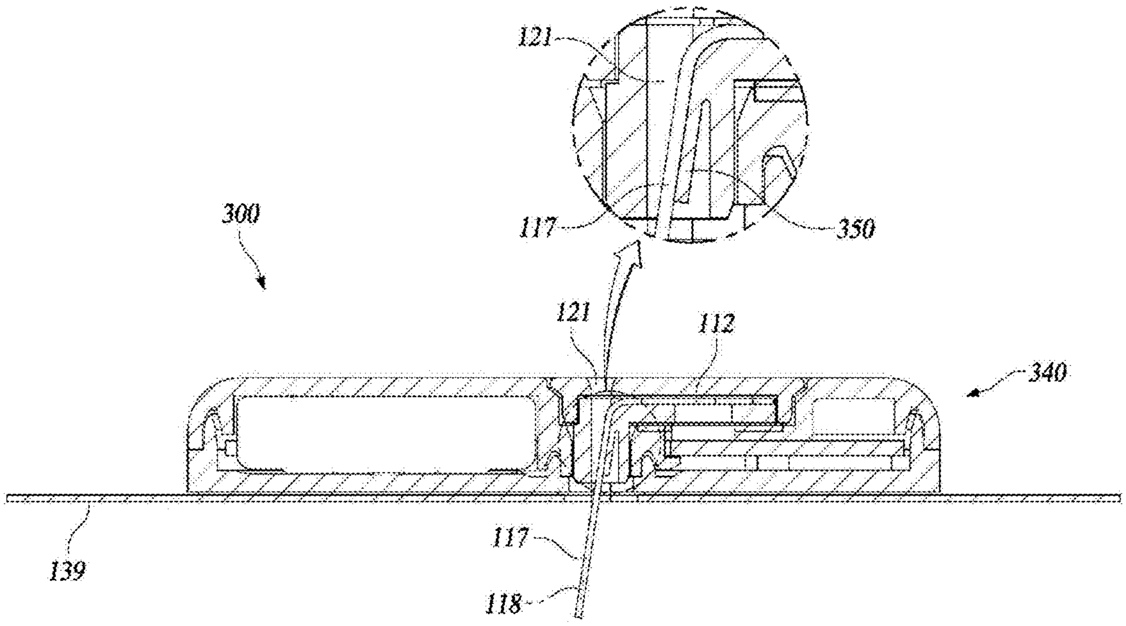

[Fig. 14]
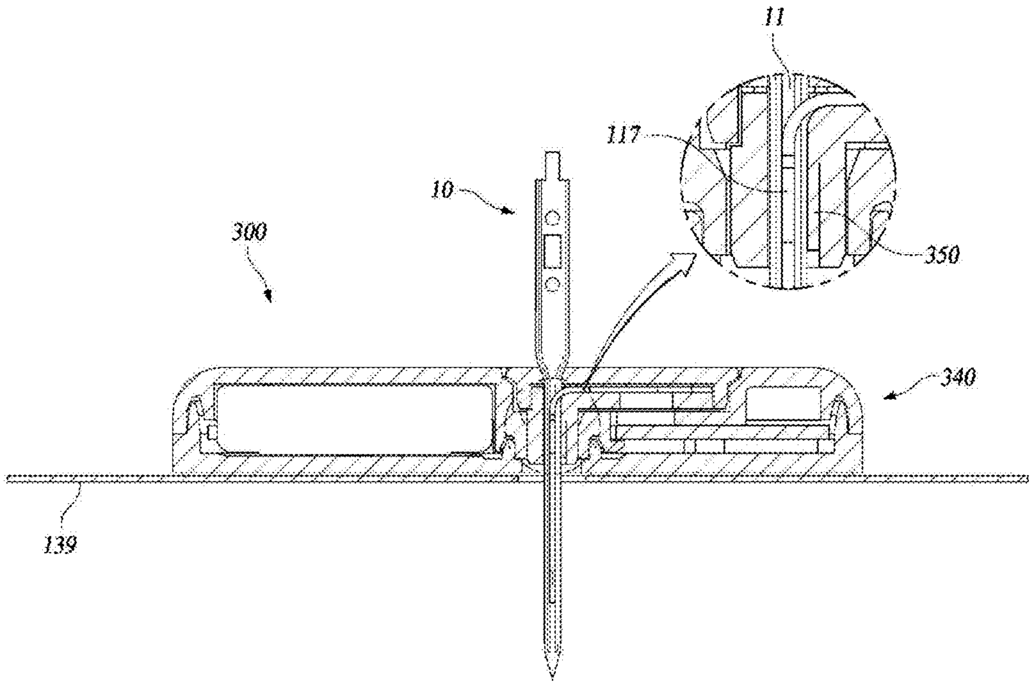
[Fig. 15]
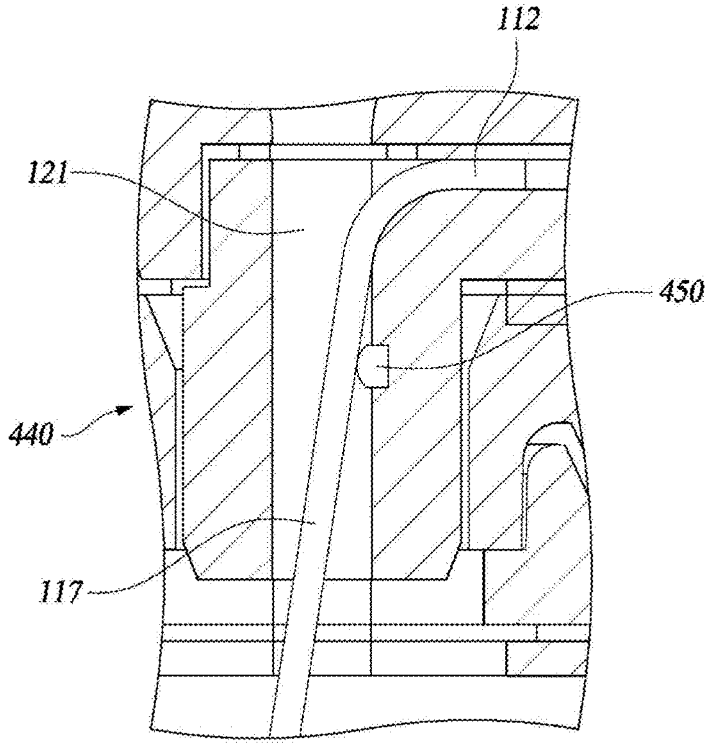

[Fig. 16]
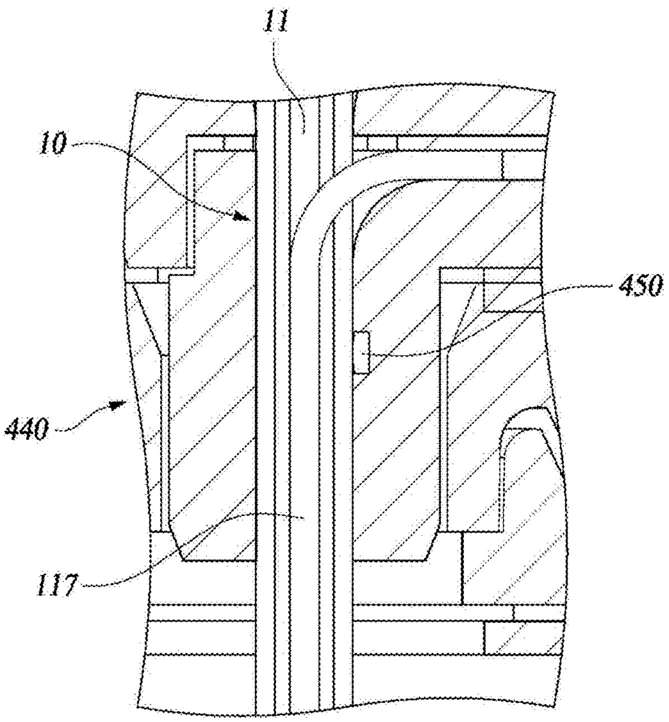
[Fig. 17]
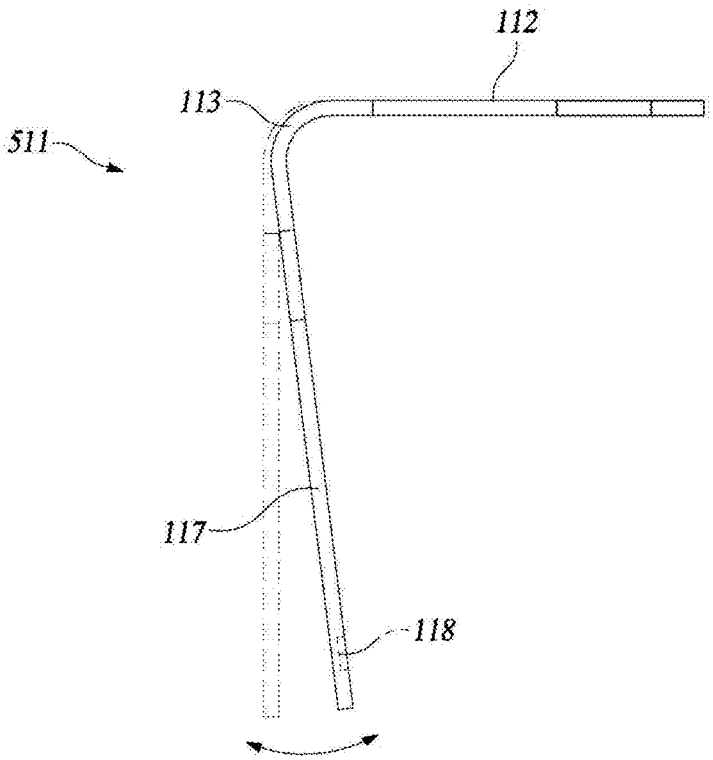

SENSOR UNIT FOR MEASURING BIOMETRIC INFORMATION

CROSS-REFERENCE TO RELATED APPLICATIONS

The present application is the U.S. National Phase of PCT Application No. PCT/KR2021/016423 filed on Nov. 11, 2021, which claims the priority to Korean Patent Application No. 10-2021-0084704 filed on Jun. 29, 2021, the entire contents of which are incorporated herein by reference.

TECHNICAL FIELD

The present disclosure relates to a sensor unit for biometric information measurement, and more specifically, to a sensor unit for biometric information measurement that is attached to the skin of a user and can measure the biometric information of a user.

BACKGROUND

With the recent advancement of medical technology, various medical devices that are attached to the body of a user have been developed and sold. Medical devices that are attached to the skin can be useful for monitoring biometric information or providing treatment by attaching them to the body of a patient with a chronic disease.

For example, chronic diseases such as diabetes require continuous management, and a body attachable unit for biometric information measurement that is attached to the body can be used to manage blood glucose levels in diabetic patients.

Diabetes is characterized by substantial absence of subjective symptoms at the beginning of the condition, when diabetes progresses, diabetes-specific symptoms such as overdrink, overeat, polyuria, weight loss, weariness, skin itchiness, and lower ability of naturally healing on injury on hands and feet are shown. Further progression of diabetes leads to complications such as visual disturbances, hypertension, kidney disease, paralysis, periodontal disease, muscle spasms and neuralgia, as well as gangrene.

In order to diagnose diabetes beforehand and manage to prevent the progression of diabetes into complications associated therewith, systematic blood glucose measurement and treatment should be performed.

For diabetes patients as well as people having higher than normal blood glucose, even though diabetes has not yet developed, medical device manufacturers offer a variety of blood glucose meters to measure blood glucose levels.

Glucose measuring devices may be categorized into a single time measurement type measuring a blood glucose level and collecting blood from a fingertip by a user every single time and a continuous measurement type attaching a glucose monitoring system to the belly or an arm of the user and continuously measuring blood glucose levels.

Diabetics patients generally experience hyperglycemia and hypoglycemia, an emergency may occur in the hypoglycemic conditions, and the patients may become unconscious or die if a hypoglycemic condition lasts for an extended period of time without the supply of glucose. Accordingly, although rapid discovery of the hypoglycemic condition is critically important for diabetics, blood-collecting type glucose monitoring devices intermittently measuring glucose have limited ability to accurately measure blood glucose levels.

Recently, to overcome such a drawback, continuous glucose monitoring systems (CGMSs) inserted into the human body to measure a blood glucose level every few minutes have been developed, and therefore easily perform the management of diabetics and responses to an emergency situation.

The continuous glucose monitoring system consists of a sensor unit that includes a transcutaneous sensor that is inserted into the skin of a user and measures blood glucose levels in the body, an electronic unit that is electrically connected to the sensor unit and generates a signal from biometric information measured by the sensor, and a terminal that receives and outputs the signal transmitted from the electronic unit. The sensor has electrodes that are inserted into the skin and can measure various biometric information from body fluids in the skin. The electrode of the sensor extends to a part which is not inserted into the skin to be electrically connected to the electronic unit, and the electronic unit can receive a measurement signal from the sensor. Since the sensor must remain inserted into the skin for a considerable period of time, the sensor is formed in a very thin and narrow microscopic shape so as not to cause pain to a user.

Typically, an applicator is used to insert the sensor into the body. The applicator includes a needle that is inserted into the skin of a user along with the sensor to insert the sensor into the skin of a user. The needle is removed from the skin of a user after the sensor is inserted into the skin of a user, leaving only the sensor inserted into the skin. In the process of inserting the sensor into the skin, a needle which is thicker than the sensor is inserted into the skin, so an incision which is larger than the width of the sensor is inevitably created in the skin.

After the needle is inserted into the skin with a sensor and then separated from the skin, an inflammatory reaction occurs around the sensor which is inserted into the skin and the wound is healed. In other words, inflammatory cells are involved in the wound area to remove harmful bacteria or necrotic tissue, and the cells that make up the skin proliferate to regenerate the damaged area.

However, it is known that this cell proliferation activity for wound healing reduces the measurement accuracy of the sensor when a sensor which is inserted into the skin measures biometric information from analyte substances in the skin, such as body fluids. Therefore, in order to increase the reliability of measurement by the sensor, it is necessary to solve measurement problems caused by the above inflammatory reaction.

SUMMARY

Technical Problem

The present disclosure is developed in consideration of the above-mentioned points, and the purpose is to provide a sensor unit for measuring biometric information that can reduce the problem in which measurement accuracy is deteriorated due to inflammatory reactions in the skin after the sensor is inserted into the skin.

Solution to Problem

To accomplish the above-described purposes, a sensor unit configured to be attachable to skin of a user to measure biometric information of a user may comprise: a sensor comprising a sensor body, an insertion portion configured to be insertable into the skin of the user by being connected to the sensor body, and a sensing portion provided at one side of the insertion portion to measure the biometric information; and a sensor unit housing to which the sensor is mounted, the sensor unit housing comprising a needle configured to be insertable into the skin of the user together with the insertion portion and an insertion hole through which the insertion portion passes, wherein the sensor unit in configured to be attachable to the skin of the user, wherein the insertion portion is configured to be insertable together with the needle into an incision portion formed at the skin of the user, and, after the needle is separated from the skin of the user, inclination with respect to the sensor body is changed to be tilted with respect to a longitudinal direction central axis of the incision portion.

The insertion portion may be configured to move to press the sensing portion toward biological tissue in the skin within the incision portion when the needle is separated from the skin of the user.

The sensor may be configured to be elastically deformable such that the sensor body and the insertion portion form an obtuse angle after the needle is separated from the skin of the user.

The sensor may include a curved shaped connection portion connecting the sensor body and the insertion portion.

The sensor may connect the sensor body and the insertion portion by being arranged to be disposed on a plane different from the sensor body and includes a middle portion having a width wider than the insertion portion.

The sensor unit housing may include an arch-shaped support portion contacting the connection portion to support the connection portion.

The sensor may be configured to elastically deformable such that the sensor body and the insertion portion form an acute angle after the needle is separated from the skin of the user.

The sensor unit according to an embodiment of the present disclosure may further comprise an elastic portion configured to be elastically deformable by the needle and provided in the sensor unit housing to apply an elastic force to the insertion portion in a direction of being inclined with respect to the longitudinal direction central axis of the incision portion when the needle is separated from the insertion hole.

The sensor may comprise a shape-memory material such that the sensor is deformable depending on a temperature change to change an angle between the sensor body and the insertion portion.

Advantageous Effects of Invention

According to the present disclosure, after the insertion portion of the sensor is inserted into the incision formed in the skin of a user by a needle, by moving the sensing portion for measuring biometric information toward undamaged biological tissue within the skin, the sensing portion can be located in an area where the proliferation of regenerative cells due to an inflammatory reaction occurs relatively less. Therefore, the sensor unit according to the present disclosure can minimize the problem in which the measurement accuracy of the sensor is deteriorated due to inflammatory reaction in the skin.

BRIEF DESCRIPTION OF THE DRAWINGS

FIG. 1 is a cross-sectional view showing a sensor unit according to an embodiment of the present disclosure.

FIG. 2 is a perspective view showing a sensor unit according to an embodiment of the present disclosure.

FIG. 3 shows a sensor unit according to an embodiment of the present disclosure attached to the skin of a user.

FIG. 4 is a perspective view showing a sensor of a sensor unit according to an embodiment of the present disclosure.

FIG. 5 is a side view showing a sensor of a sensor unit according to an embodiment of the present disclosure.

FIGS. 6 to 8 show a method of attaching the sensor unit to the skin of a user according to an embodiment of the present disclosure.

FIG. 9 shows the sensor of the sensor unit according to an embodiment of the present disclosure inserted into the skin of a user.

FIGS. 10 to 12 show a method of attaching a sensor unit to a user's skin according to another embodiment of the present disclosure.

FIGS. 13 and 14 show a sensor unit according to another embodiment of the present disclosure.

FIGS. 15 and 16 are cross-sectional views showing a portion of a sensor unit according to another embodiment of the present disclosure.

FIG. 17 is a side view showing a modified example of the sensor.

DETAILED DESCRIPTION OF EMBODIMENTS

Hereinafter, the sensor unit for biometric information measurement according to the present disclosure will be described in detail with reference to the drawings.

FIG. 1 is a cross-sectional view showing a sensor unit according to an embodiment of the present disclosure, FIG. 2 is a perspective view showing a sensor unit according to an embodiment of the present disclosure, and FIG. 3 is a sensor unit according to an embodiment of the present disclosure attached to the skin of a user.

As shown in the drawing, the sensor unit (100) according to an embodiment of the present disclosure can be attached to the skin of a user and measure biometric information. The sensor unit (100) may be attached to the skin of a user (S) by an applicator (not shown) and then transmit the measured biometric information to an external terminal (20) or the like. The external terminal (20) may be a variety of devices capable of receiving measurement data from the sensor unit 100, such as a user's portable terminal, a medical device, a PC, or a server. Biometric information that the sensor unit (100) can measure is not limited to specific information. For example, the sensor unit (100) may periodically measure the blood glucose level of a user The sensor unit (100) includes a sensor module (110) for measuring the biometric information of a user, and a base module (130) that is attached to the skin of a user and coupled to the sensor module (110). The base module (130) may have electronic components installed therein. This base module (130) is electrically connected to the sensor module (110) and can process biometric information measured by the sensor module (110) and transmit it to an external terminal (20) or the like. The sensor module (110) and the base module (130) may be mounted within the applicator to be spaced apart from each other. The applicator is provided with a needle (10) for inserting the sensor (111) of the sensor module (110) into the skin of a user (S), and operates to couple the sensor module (110) and the base module (130) to form the sensor unit (100), thereby attaching the sensor unit (100) to the skin of a user.

The sensor module (110) includes a sensor (111) inserted into the skin of a user, a sensor module housing (120) to which the sensor (111) is coupled and a sensor module terminal portion (124) is coupled to the sensor module housing (120) and electrically connected to the sensor (111).

The sensor (111) includes a sensor body (112), a connection portion (113) connected to one side of the sensor body (112), a middle portion (114) connected to the sensor body (112) through the connection portion (113) and an insertion portion (117) connected to the middle portion (114) to be inserted into the skin of a user. The sensor body (112) is disposed inside the sensor module housing (120) so as to contact the sensor module terminal portion (124). The sensor body (112) may be provided with an electrode electrically connected to the sensor module terminal portion (124). The connection portion (113) extends from the edge of the sensor body (112) and connects the sensor body (112) and the middle portion (114) to lie on different planes. The sensor (111) is manufactured in the form of a plate in which the sensor body (112) lies on the same plane as the connection portion (113), the middle portion (114), and the insertion portion (117), and then the connection portion (113) is bent and deformed so that the sensor body (112) lies on a different plane from the middle portion (114) and the insertion portion (117).

The middle portion (114) and the insertion portion (117) are connected to the sensor body (112) so as to lie on a different plane from the sensor body (112). In the drawing, the middle portion (114) and the insertion portion (117) are shown to be disposed on the same plane, and the middle portion (114) is disposed at an obtuse angle with the sensor body (112), but the angle between the middle portion (114) and the sensor body (112) or the angle between the insertion portion (117) and the sensor (body) 112 can be changed in various ways. The middle portion (114) includes a first extension portion (115) that protrudes from one side of the connection portion (113), and a second extension portion (116) protruding from the connection portion (113) in a direction opposite to the direction in which the first extending portion (115) protrudes from the connection portion (113).

The insertion portion (117) may be connected to the first extension portion (115) and inserted into the skin of a user. The insertion portion (117) has a relatively thin and long shape so that it can be smoothly inserted into the skin of a user. A sensing portion (118) for measuring biometric information is provided on one side of the insertion portion (117). The sensing portion (118) may be configured to include an electrode that can generate an electrical signal by contacting an analyte such as body fluid in the skin (S). As shown, the sensing portion (118) may be disposed biased toward the end of the insertion portion (117). Additionally, the sensing portion (118) is disposed on the side far from the sensor body (112) among both sides of the insertion portion (117). The sensing portion (118) may be electrically connected to the electrode of the sensor body (112) through a conductive trace provided in the sensor body (112), the connection portion (113), the middle portion (114), and the insertion portion (117).

The sensor (111) may be coupled to the sensor module housing (120) so that the sensor body (112), the connection portion (113), and the middle portion (114) are located inside the sensor module housing (120), and only the insertion portion (117) protrudes from the sensor module.

Additionally, the sensor (111) may be elastically deformed so that the angle between the sensor body (112) and the insertion portion (117) can be changed. As shown in FIG. 5, in the sensor (111), the inclination of the insertion portion (117) with respect to the sensor body (112) may be changed in a way in which the connection portion (113) is elastically deformed. The sensor (111) may be manufactured so that the sensor body (112) and the insertion portion (117) form an obtuse angle. The sensor (111) may be elastically deformed so that the angle between the sensor body (112) and the insertion portion (117) is reduced from the original angle when the insertion portion (117) is coupled with the needle (10), and after the insertion portion (117) is inserted into the skin of a user (S), the angle between the sensor body (112) and the insertion unit (117) may be restored to its original angle. The insertion portion (117) may be coupled to the needle (10) coupled to the sensor module housing (120) and inserted into the skin of a user (S) with the needle (10).

In addition to the configuration shown, the sensor (111) may be changed into various other forms including a sensor body (112) and an insertion portion (117) connected to the sensor body (112) so as to be inserted into the skin of a user (S). As another exemplary embodiment, the sensor may be configured such that the middle portion is omitted, or the insertion portion is directly connected to the sensor body without a connection portion.

The needle (10) may be inserted into the skin of a user (S) by moving together with the sensor module (110) while being coupled to the sensor module (110), thereby inserting the insertion portion (117) into the skin of a user (S). The needle (10) may retreat after the insertion portion (117) is inserted into the skin (S) and be separated from the skin of a user (S) and the sensor module (110). Needle (10) has a channel (11) capable of receiving an insertion portion (117). The channel (11) has a shape extending parallel to the longitudinal central axis (An) of the needle (10). The insertion portion (117) is inserted into the channel (11) and arranged parallel to the longitudinal central axis (An) of the needle (10). Since the needle (10) is coupled to the sensor module housing (120) and disposed approximately perpendicular to the sensor body (112), the insertion portion (117) may be accommodated in the channel (11) of the needle (10) while being substantially perpendicular to the sensor body (112).

The sensor module housing (120) can accommodate the sensor body (112) of the sensor (111), the connection portion (113), the middle portion (114), and part of the insertion portion (117). In the middle of the sensor module housing (120), an insertion hole (121) through which the insertion portion (117) of the sensor (111) and the needle (10) can pass is formed to penetrate the sensor module housing (120) in the thickness direction. Inside the sensor module housing (120), a support portion (122) is provided to support the connection portion (113) of the sensor (111). The support portion (122) may be formed in an arch shape corresponding to the connection portion (113) so as to stably support the connection portion (113) by making surface contact with the curved connection portion (113). An adhesive layer (126) is provided on the surface of the sensor module housing (120). The sensor module housing (120) may be attached to the base module (130) by an adhesive layer (126).

The sensor module housing (120) may be coupled to the base module (130) in various other ways than using the adhesive layer (126) as shown.

The sensor module terminal portion (124) is disposed in the sensor module housing (120) to be electrically connected to the sensor body (112) of the sensor (111). The sensor module terminal portion (124) may be electrically connected to the base module (130) by partially exposing the sensor module housing (120) to the surface. The sensor module terminal portion (124) may contact the base module terminal portion (137) of the base module (130) to electrically connect the sensor (111) to the base module (130).

The base module (130) includes a base module housing (131) to which the sensor module (110) is coupled, and electronic components installed inside the base module housing (131). Electronic components may include a circuit board (136), a base module terminal (137) in contact with the sensor module terminal (124) of the sensor module (110), a battery (138), etc. The circuit board (136) may be equipped with a processor chip for processing signals or a communication chip for wireless communication with the external terminal (20).

The base module housing (131) is provided with a through hole (132) through which the insertion portion (117) of the sensor (111) and the needle (10) can pass, and a recess (133) into which the sensor module housing (120) is coupled. Inside the recess (133), a contact surface (134) to which the adhesive layer (126) of the sensor module (110) is adhered is provided. An adhesive portion (139) is provided on the surface of the base module housing (131). The adhesive portion (139) is attached to the skin of a user (S) and can adhere the base module housing (131) to the skin of a user (S). A hole is formed in the middle of the adhesive portion (139) through which the insertion portion (117) of the sensor (111) and the needle (10) can pass. The base module housing (131) forms the sensor unit housing (140) together with the sensor module housing (120).

The base module terminal portion (137) is disposed to be exposed on the contact surface (134) and contacts the sensor module terminal portion (124) of the sensor module (110) when the sensor module (110) is coupled to the base module (130). The base module terminal portion (137) may be electrically connected to the circuit board (136).

FIGS. 6 to 8 show a method of attaching the sensor unit (100) according to an embodiment of the present disclosure to the skin of a user (S).

The sensor unit (100) according to an embodiment of the present disclosure is mounted on an applicator so that the sensor module (110) and the base module (130) are spaced apart from each other, and can be attached to the skin of a user by the applicator in a state in which the sensor module (110) and the base module (130) are coupled. In order to attach the sensor unit (100) to the skin of a user (S) using an applicator, as shown in FIG. 6, first, the base module (130) is attached to the skin of a user (S) using the adhesive portion (139). The sensor module (110) stands by at a location spaced apart from the base module (130) while being coupled to the needle (10). The needle (10) is coupled to the sensor module (110) so as to be approximately perpendicular to the sensor body (112) by being inserted into the insertion hole (121) of the sensor module housing (120), and the insertion portion (117) of the sensor (111) is inserted into the channel (11) of the needle (10). The insertion portion (117) may be inserted into the channel (11) such that its longitudinal central axis (As) is parallel to the longitudinal central axis (An) of the needle (10). In the process of coupling the sensor (111) and the needle (10) so that the insertion portion (117) is accommodated in the channel (11), the sensing portion (118) may be elastically deformed so that the sensor body (112) and the insertion portion (117) are substantially perpendicular by elastically deformed the connection portion (113).

As shown in FIG. 7, as the applicator operates, the sensor module (110) moves and is coupled to the base module (130). At this time, the sensor module (110) and the base module (130) are adhered by the adhesive layer (126), and the needle (10) and the insertion portion (117) are inserted into the skin of a user (S). In the process of inserting the needle (10) and the sensor (111) into the skin (S), the needle (10) forms a incision portion (C) in which the insertion portion (117) is accommodated in the skin (S) by penetrating the skin tissue and entering the skin (S). The width of the incision portion (C) formed by the needle (10) is larger than the width of the insertion portion (117). The insertion portion (117) may be inserted into the incision portion (C) by moving in a direction parallel to the longitudinal central axis (An) of the needle (10) while being inserted into the channel (11) of the needle (10).

After the insertion portion (117) is inserted into the skin (S), the needle (10) is separated from the skin (S) and the sensor unit (100), as shown in FIG. 8. Since the sensor (111) is inserted into the skin (S) in a state in which the insertion portion (117) was elastically deformed by the needle (10) so as to be approximately perpendicular to the sensor body (112), the insertion portion (117) may be tilted by the elastic force of the sensor (111) itself when the needle (10) is separated from the skin (S).

Therefore, as shown in FIGS. 8 and 9, after the insertion portion (117) is inserted into the incision portion (C), its inclination with respect to the sensor body (112) is changed so that the longitudinal central axis (As) is inclined with respect to the longitudinal central axis (Ac) of the incision portion (C). At this time, the insertion portion (117) moves to form an obtuse angle with the sensor body (112) in the incision portion (C) for the sensing portion (118) to be eccentric with respect to the longitudinal central axis (Ac) of the incision portion (C) and press toward the undamaged biological tissue (T) in the skin.

Meanwhile, an inflammatory reaction occurs in the skin (S) where the insertion portion (117) is inserted. That is, in the incision (C) formed when the skin tissue is destroyed by the needle (10), inflammatory cells are involved to remove harmful bacteria or necrotic tissue, and the cells constituting the skin proliferate to regenerate the damaged area. By this regenerative activity of the skin for wound treatment, regenerative cells (R) proliferate in the incision portion (C). Proliferation of regenerative cells (R) around the insertion portion (117) may reduce the measurement efficiency of the sensor (111).

However, the sensor unit (100) according to an embodiment of the present disclosure inserts the insertion portion (117) of the sensor (111) into the incision portion (C), and then moves the sensing portion (118) toward the undamaged biological tissue (T) in the skin, thereby positioning the sensing portion (118) in an area where the proliferation of regenerative cells (R) appears relatively less. Therefore, in the incision portion (C), as the proliferation of regenerative cells (R) occurs more actively on the other side of the insertion portion (117) than on one side of the insertion section (117) where the sensing portion (118) is placed, the damage area of the skin (S) is healed. Through this action, the sensor unit (100) according to an embodiment of the present disclosure can minimize the problem of deterioration of the measurement accuracy of the sensor (111) due to an inflammatory reaction in the skin.

Meanwhile, FIGS. 10 to 12 show a method of attaching a sensor unit to the skin of a user according to another embodiment of the present disclosure.

The sensor unit (200) according to another embodiment of the present disclosure is manufactured not in a form in which, like the sensor unit (100) described above, the sensor module (110) having the sensor (111) and the base module (130) having the electronic component installed are separated, but in a form in which the sensor (111) and various electronic components are mounted in one sensor unit housing (240). The sensor unit (200) may be mounted on an applicator and attached to the skin of a user (S) by the applicator.

A method of attaching the sensor unit (200) according to another embodiment of the present disclosure to the skin of a user (S) is as follows.

In order to attach the sensor unit (200) to the skin of a user (S) using an applicator, the sensor unit (200) is mounted on the applicator so that the needle (10) is coupled to the sensor unit (200). At this time, the needle (10) is inserted into the insertion hole (221) of the sensor unit housing (240) and coupled to the sensor unit (200) so as to be approximately perpendicular to the sensor body (112). At this time, the sensor (111) is elastically deformed so that the insertion portion (117) is substantially perpendicular to the sensor body (112).

When the applicator is placed on the skin of a user (S) so that the adhesive portion (139) faces the skin of a user (S) and the applicator is operated, as shown in FIG. 11, the sensor unit (200) is adhered to the skin of a user by the adhesive portion (139), and the needle (10) and the insertion portion (117) are inserted into the skin of a user (S). In the process of inserting the needle (10) and the sensor (111) into the skin (S), as the needle (10) penetrates the skin tissue and enters the skin (S), the insertion portion (117) is inserted into the incision portion (C) formed by the needle (10) in the skin (S).

Thereafter, as shown in FIG. 12, the needle (10) is separated from the skin (S) and the sensor unit (200). After the needle (10) is separated from the skin (S), the movement of the insertion portion (117) is the same as described above. That is, when the needle (10) is separated from the skin (S), the supporting force of the needle (10) supporting the insertion portion (117) is removed, and the insertion portion (117) moves to form an obtuse angle with the sensor body (112) in the incision portion (C). Therefore, the sensing portion (118) is eccentric from the longitudinal central axis (Ac) of the incision portion (C) and is positioned toward the undamaged biological tissue (T) in the incision portion (C), and through this action, the problem of deterioration in the measurement accuracy of the sensor (111) due to an inflammatory reaction can be minimized.

Meanwhile, FIGS. 13 and 14 show a sensor unit according to another embodiment of the present disclosure.

The sensor unit (300) shown in FIGS. 13 and 14 has a slightly modified configuration of the sensor unit housing (340) compared to the sensor unit (100) shown in FIG. 1.

The sensor unit housing (340) is provided with an elastic portion (350) that can contact the insertion portion (117) of the sensor (111) in the insertion hole (121). The elastic portion (350) may be elastically deformed when the needle (10) is inserted into the insertion hole (121), and when the needle (10) is separated from the insertion hole (121), an elastic force may be applied to the insertion portion (117) by contacting the insertion portion (117). The elastic portion (350) may apply an elastic force to the insertion portion (117) in a direction inclined with respect to the longitudinal central axis (Ac) of the incision portion (C) after the needle (10) is separated from the insertion hole (121).

As shown in FIG. 14, in a state in which the needle (10) is coupled so as to the sensor unit housing (340) to surround the insertion portion (117), the elastic portion (350) is elastically deformed by being pressed by the needle (10). When the needle (10) and the insertion portion (117) are inserted into the skin of a user and the needle (10) is separated from the sensor unit housing (340), the elastic portion (350) is returned to its original state. At this time, the elastic portion (350) presses the insertion portion (117) so that the insertion portion (117) moves within the skin of a user and presses the sensing portion (118) toward undamaged biological tissue.

In this embodiment, the sensor (111) may be manufactured in a form where the sensor body (112) and the insertion portion (117) form an obtuse angle, as described above. At this time, the insertion portion (117) can be tilted more smoothly in the skin of a user by the elastic force of the sensor (111) itself and the elastic force applied by the elastic portion (350).

As another exemplary embodiment, the sensor (111) may be configured so that the insertion portion (117) can be tilted with respect to the sensor body (112) only when the elastic force of the elastic portion (350) acts. In this case, the sensor (111) may be manufactured in a form where the sensor body (112) and the insertion portion (117) form a right angle or another angle.

Meanwhile, FIGS. 15 and 16 are cross-sectional views showing a portion of a sensor unit according to another embodiment of the present disclosure.

The sensor unit shown in FIGS. 15 and 16 has a modified elastic portion (450) provided in the sensor unit housing (440) compared to the sensor unit (300) described above.

The elastic portion (450) is provided in the sensor unit housing (440) so as to be in contact with the insertion portion (117) in the insertion hole (121) and apply an elastic force to the insertion portion (117). The elastic portion (450) may be made of an elastically deformable material capable of applying an elastic force to the insertion portion (117) by being elastically deformed by the needle (10) and returning to its original state when the needle (10) is separated from the insertion hole (121).

As shown in FIG. 16, the elastic portion (450) may be compressed when the needle (10) is inserted into the insertion hole (121). Additionally, the elastic portion (450) may expand to its original state when the needle (10) is separated from the insertion hole (121) and apply an elastic force to the insertion portion (117).

The elastic portion that can apply elastic force to the insertion portion (117) so that the insertion portion (117) is tilted within the skin of a user may be modified into various other forms other than the illustrated form. Additionally, the installation location of the elastic portion can be changed in various ways. Additionally, depending on the shape of the elastic portion or the shape of the sensor (111), the location of the part in contact with the elastic portion in the sensor (111) may be changed to a different location.

Meanwhile, FIG. 17 is a side view showing a modified example of the sensor.

The sensor (511) shown in FIG. 17 is manufactured so that the sensor body (112) and the insertion portion (117) form an acute angle. That is, the sensor (511) may be manufactured in an elastically deformable form so that the sensor body (112) and the insertion portion (117) form an acute angle after the insertion portion (117) is inserted into the skin of a user. The sensing portion (118) is disposed on one side of both sides of the insertion portion (117) that is closer to the sensor body (112). The sensor (511) may be elastically deformed so that the insertion portion (117) and the sensor body (112) are substantially perpendicular when the insertion portion (117) is coupled to the needle (10). When the needle (10) is separated from the skin of a user, the insertion portion (117) moves by the elastic force of the sensor (111) itself to press the sensing portion (118) toward undamaged biological tissue in the skin.

Although the present disclosure has been described above with preferred examples, the scope of the present disclosure is not limited to the form described and shown above.

For example, the sensor may not be in an elastically deformable form, but may take on a variety of other configurations such that the insertion portion can be moved to change its tilt relative to the sensor body after being inserted into the skin of a user. As another exemplary embodiment, the sensor may include a shape memory material so that its shape can change with temperature changes. After the insertion portion is inserted into the skin of a user, the sensor can move so that the inclination of the insertion portion with respect to the sensor body changes by being deformed by the user's body temperature.

Additionally, as another exemplary embodiment, the base module may simply support the sensor module so that it is not separated from the skin of a user. In this case, a separate electronic module that can process biometric information measured by the sensor module and transmit it to an external terminal, etc. may be detachably coupled to the base module. A separate electronic module may be coupled to the base module to be electrically connected to the sensor module after the sensor module is coupled to the base module. The sensor unit including this base module can be used by coupling with a separate electronic module.

As described above, although the present disclosure has been shown and described in connection with preferred embodiments for illustrating the principles of the disclosure, the disclosure is not limited to the construction and operation as shown and described. Rather, those skilled in the art will understand that numerous changes and modifications can be made to the present disclosure without departing from the concepts and scopes of the appended claims.

What is claimed is:

1. A sensor unit configured to be attachable to skin of a user to measure biometric information of a user, the sensor unit comprising:

a sensor comprising a sensor body, an insertion portion configured to be insertable into the skin of the user by being connected to the sensor body, and a sensing portion provided at one side of the insertion portion to measure the biometric information; and a sensor unit housing to which the sensor is mounted, the sensor unit housing comprising a needle configured to be insertable into the skin of the user together with the insertion portion and an insertion hole through which the insertion portion passes, wherein the sensor unit is configured to be attachable to the skin of the user, wherein the insertion portion is configured to be insertable together with the needle into an incision portion formed at the skin of the user, and, after the needle is separated from the skin of the user, an inclination of the insertion portion with respect to the sensor body is changed to be tilted with respect to a longitudinal direction central axis of the incision portion.

2. The sensor unit according to claim 1, wherein the insertion portion is configured to move to press the sensing portion toward biological tissue in the skin within the incision portion when the needle is separated from the skin of the user.

3. The sensor unit according to claim 2, wherein the sensor is configured to be elastically deformable such that the sensor body and the insertion portion form an obtuse angle after the needle is separated from the skin of the user.

4. The sensor unit according to claim 3, wherein the sensor includes a curved shaped connection portion connecting the sensor body and the insertion portion.

5. The sensor unit according to claim 4, wherein the sensor connects the sensor body and the insertion portion by being arranged to be disposed on a plane different from the sensor body and includes a middle portion having a width wider than the insertion portion.

6. The sensor unit according to claim 4, wherein the sensor unit housing includes an arch-shaped support portion contacting the connection portion to support the connection portion.

7. The sensor unit according to claim 2, wherein the sensor is configured to elastically deformable such that the sensor body and the insertion portion form an acute angle after the needle is separated from the skin of the user.

8. The sensor unit according to claim 1, further comprising an elastic portion configured to be elastically deformable by the needle and provided in the sensor unit housing to apply an elastic force to the insertion portion in a direction of being inclined with respect to the longitudinal direction central axis of the incision portion when the needle is separated from the insertion hole.

9. The sensor unit according to claim 1, wherein the sensor comprises a shape-memory material such that the sensor is deformable depending on a temperature change to change an angle between the sensor body and the insertion portion.

* * * * *